(12) United States Patent
Seki

(10) Patent No.: US 6,475,716 B1
(45) Date of Patent: Nov. 5, 2002

(54) METHOD FOR PRESERVING MAMMALIAN ORGANS

(75) Inventor: Kunihiro Seki, Kanagawa-ken (JP)

(73) Assignee: Biobank Co., Ltd., Kanagawa-ken (JP)

( * ) Notice: Subject to any disclaimer, the term of this patent is extended or adjusted under 35 U.S.C. 154(b) by 0 days.

(21) Appl. No.: 09/799,112

(22) Filed: Mar. 6, 2001

(51) Int. Cl.$^7$ .............................. A01N 1/00; A01N 1/02
(52) U.S. Cl. .......................... 435/1.3; 435/1.1; 435/1.2
(58) Field of Search ............................. 435/1.1, 1.2, 1.3

(56) References Cited

U.S. PATENT DOCUMENTS 5,066,578 A * 11/1991 Wikman-Coffelt ............. 435/1

FOREIGN PATENT DOCUMENTS

| JP | 12295398 | 4/1998 |
| JP | 11289917 | 10/1999 |
| JP | 200072601 | 3/2000 |

OTHER PUBLICATIONS

Blakiston's Gould Medical Dictionary, Fourth Edition, 1979, p. 1262.*
J. D. Cooper et al., *J. Thoracic and Cardiovascular Surgery,* vol. 107, No. 2, pp. 460–471 (Feb. 1994).
L. Makowka et al., *Tranplant Proceedings,* vol. 21, No. 1, pp. 1350–1352 (Feb. 1989).
T. Yeh, Jr. et al., *Ann Thorac Surg,* 49:932–9 (1990).
Y. Kuroda et al., *Transplantation,* vol. 59, No. 5, pp. 699–701 (Mar. 1995).
D. E. Pegg, *Surgical Clinics of North America,* vol. 66, No. 3, pp. 617–632, (Jun. 1986).
M. C. Oz et al., *Circulation,* vol. 88, No. 5, Part 2, pp. II292–II–297 (Nov. 1993).
J. E. Heffner et al., *Am Rev Respir Dis,* 140:531–554 (1989).
K. Seki et al., *Nature,* vol. 395, No. 6705, pp. 853–854 (Oct. 1998).
M. Kalayoglu et al., *The Lancet,* pp. 617–619, (Mar. 19, 1988).
J. H. Crowe et al., *Science,* vol. 223, pp. 701–703, (Feb. 1984).
A. Wiemken, *Antonie van Leeuwenhoek,* 58:209–217 (1990).
J. C. Stringham et al., *Transplantation,* vol. 53, No. 2, pp. 287–294 (Feb. 1992).
T. Hirata et al., *Surgery,* vol. 115, No. 1, pp. 102–107 (Jan. 1994).
J. H. Crowe et al., *Biochem J.,* vol. 242, pp. 1–10 (1987).
Bailey, L. E., "Preservation of guinea pig hearts. . . ", *Can. J. Physiol. Pharmacol.,* vol. 67, No. 7, 1989, pp. 692–696.*
Guo, et al., Trehalose expression confers desiccation. . . ", *Nature Biotechnology,* vol. 18, No. 2, 2000, pp. 168–171.*
Urushihara, et al., "A Comparison of Rat Pancreas Preservation. . . ", *Transplantation Proceedings,* vol. 30, No. 7, 1998, pp. 3425–3426.*

* cited by examiner

*Primary Examiner*—Sandra E. Saucier
*Assistant Examiner*—Vera Afremova
(74) *Attorney, Agent, or Firm*—Birch, Stewart, Kolasch & Birch, LLP

(57) ABSTRACT

The method of the invention for preserving mammalian organs comprises two steps, one being the step of dehydration in which an organ having a physiologically normal water content is deprived of water in an amount of at least about 25% by weight of the total weight of the organ before dehydration such that water is left intact in an amount of at least from about 10 to about 20% by weight of the total content of water before dehydration, the step of dehydration being followed by the step of immersing the dehydrated organ in an inert medium and maintaining it at a chill temperature.

13 Claims, 4 Drawing Sheets

METHOD FOR PRESERVING MAMMALIAN ORGANS

CROSS REFERENCE TO RELATED APPLICATION

Japanese Patent Public Disclosure No. 72601/2000: This application was filed with the Japanese Patent Office on Aug. 31, 1998 as Japanese Patent Application No. 245052/1998. The title of the invention was "a method for preserving extracted mammalian organs" and the inventor was Kunihiro Seki, D. Sc., the same as the inventor of the present invention. The application was laid open to public inspection in Japan on Mar. 7, 2000 and is incorporated herein by reference to the specification and the drawings.

BACKGROUND OF THE INVENTION

1. Technical Field of the Invention

The present invention relates to a method for prolonged storage of extracted mammalian organs and such organs that have been preserved for use in transplants.

2. Prior Art

Clinical transplants of human organs such as lungs, heart, liver, kidneys and pancreas are routinely performed today. However, as the number of patients waiting for organ transplants increases yearly, the shortage of donors has become a serious problem and the waiting time to surgery is also increasing. Even if a donor is found, his or her organs cannot be effectively used in transplants since nothing like blood banks exist for organs that are fully equipped with the ability to preserve organs for prolonged periods and allow for efficient supply of organs.

Organs to be transplanted are most commonly preserved by cold storage but the preservation limit is about 4–24 hours (Cooper J D, Patterson G A, Trulock E P et al.; J. Thorac. Cardiovasc. Surg. 107, 460–471, 1994). In experiments using University of Wisconsin Solution (UWS) as a medium for cold storage of hearts from rats, rabbits and baboons before resuscitation, the time limit was 6–18 hours (Makowka I, Zerbe T R, Champman F et al.; Transplant Proc. 21, 1350, 1989 and Yen T, Hanan S A, Johnson D E et al.; Ann. Thorac. Surg. 49, 932, 1990). Transplanting of rat hearts (n=5) immersed in a combination medium of UWS and perfluorocarbon was found to be successful at both 24 hours (100%) and 48 hours (4 out of the 5 animals) (Kuroda Y, Kawamura T, Tanioka T et al; Transplantation, 59, 699–701, 1995). The reason for these short time limits is that when removed hearts are exposed to the low temperature of 4° C. or ischemic injury, their cell membranes are damaged to make tissue cell resuscitation impossible (Pegg D E; Organ Preservation Surg. Clin. North Am. 66, 617, 1986: Oz M C, Pinsky D J, Koga S et al.; Circulation 88, 291–297, 1993: and Heffner J E, Pepine J E; Rev. Pespir. Dis. 140, 531–554, 1989).

The technology for storing mammalian living tissues over prolonged periods before resuscitation have seen marked advances only in the area of single cells such as blood, sperm and ova. Efforts to develop practically feasible methods for the cold storage of living tissues which are aggregates of cells and organs which are composed of several tissues are also in progress but they have to meet the inexorable requirement that transplant be performed within 24 hours of storage (Kalayoglu M, Sollinger H W, Strarra R J et al.; Lancet 2, 617, 1988).

As regards the technology of organ preservation and resuscitation, trehalose ($C_{12}H_{22}O_{11}$) is an interesting substance to mention. This is a nonreducing disaccharide found widely in nature and it has been reported to have the ability to stabilize or protect the structure of cell membranes under various types of stress (Crowe J H, Crowe L M, Chapman D; Science 233, 701–703, 1984 and Wiemken A; Antinei Van Leeunwenhoek 58, 209–217, 1990). It was also reported that trehalose had the ability to protect cell membranes of the heart when it was exposed to the low temperature of 4° C. or ischemic injury (Stringham J C, Southhard J H, Hegge J et al.; Transplantation 58, 287–294, 1992 and Hirata T, Fukuse T, Liu C J et al.; Surgery 115, 102–107, 1994).

According to reports of experiments with tardigrades under high hydrostatic pressure, trehalose increased 10–20 fold in an anhydrous state (Crowe J H, Crowe L M, Chapman D; Science 233, 701–703, 1984 and Crowe J H, Crowe L M, Chapman D, Aurell Wistorm; Biochemical Journal 242, 1–10, 1987). Tardigrades are multicellular organisms composed of ca. 40,000 cells including nerve cells.

The present inventor previously found that tardigrades in a desiccation state had the viability to withstand high hydrostatic pressures up to 600 MPa (Kunihiro Seki et al.; Nature Vol. 395, No. 6705, pp. 853–854, Oct. 29, 1998 and Japanese Patent Public Disclosure No. 289917/1999 which is incorporated herein by reference to the specification and the drawings). Tardigrades become "desiccate" when they are in the "tun" state. The physiological mechanism behind their tun state has not been fully unravelled but it is at least clear that desiccated tardigrades have lost an extremely large amount of water in their body to become dehydrated.

SUMMARY OF THE INVENTION

As described above, the shortage of donors and the increasing time for which patients have to wait before surgery are two serious problems with organ transplants and a strong need exists to develop feasible techniques for preserving organs and later resuscitating them.

In the conventional storage of organs by refrigeration, the temperature of the organ is lowered so that its metabolism is suppressed to a level that maintains its viability. While the metabolism of the organ is suppressed by reducing temperature, water as a polar medium is a rich supply of ions which cause self-disintegration of cells, their death and necrosis over time. Hence, the longer the period of storage by refrigeration, the higher the frequency of the occurrence of serious thrombus formation and dysfunction. Organs cannot be stored cold for an indefinite period.

An object, therefore, of the invention is to provide a novel technique by which organs can be stored in vitro for a significantly increased number of days while preventing their cells and tissues from undergoing self-disintegration over time.

Another object of the invention is to provide a basic technique of such substantial utility that it can extend the duration of preservation of mammalian organs for use in transplanting into humans.

The present inventor found that the ability of desiccated tardigrades to withstand extreme environments in an inert medium could be applied to the purpose of preserving mammalian organs for an extended period. The organs preserved by the present invention can be later resuscitated for collecting viable nerves or stem cells. The resuscitated organs or the collected tissues can be used in transplants. For histopathological studies, it is quite significant that resuscitable biomaterials rather than necrotic specimens can be stored for a long period.

Animal tissue cells generally are not viable in the absence of water. One may readily imagine that organs of higher animals which are composed of heterogeneous tissues can never be resuscitated from a desiccation state. Techniques for preserving plants and various bacteria in a desiccation or dry state have already been developed but not a single experiment has been reported in which organs of higher animals were successfully resuscitated after storage in a desiccation or dry state.

To his surprise, the present inventor found that when extracted mammalian organs were deprived of much water under specified conditions and later stored at low temperature within an inert medium, they had apparent death of the same nature as experienced by tardigrades which remained viable in the tun state for a prolonged period.

Particularly surprising was that multi-cell and multi-tissue mammalian organs resuscitated from an extremely dehydrated state and that the resuscitated heart was found to beat. The cells of the resuscitated organ are believed to be in apparent death characterized by either an extreme drop in oxygen consumption (no greater than $\frac{1}{1000}$ of the normal level) or substantial arrest of oxygen consumption.

The method for preserving mammalian organs according to the first aspect of the invention comprises two steps, one of dehydrating an organ to remove water but leave intact an amount of water that permits later resuscitation and the other of immersing the organ in an inert medium and maintaining it at a chill temperature or below.

In a preferred case of the dehydration step, an organ having a physiologically normal water content is deprived of water in an amount of at least about 25% by weight of the total weight of the organ before dehydration such that water is left intact in an amount of at least from about 10 to about 20% by weight of the total content of water before dehydration. This step of dehydration is preferably followed by the step of immersing the organ in an inert medium and maintaining it at a chill temperature.

The preserved mammalian organ according to the second aspect of the invention is such that it is deprived of water in an amount of at least about 25% by weight of its physiologically normal, total weight while leaving water intact in an amount of at least from about 10 to about 20% by weight of the total water content in the organ which is then immersed in an inert medium and maintained at a chill temperature or below. Examples of such stored mammalian organs include heart, liver, kidneys, pancreas and lungs.

"Depriving of water in an amount of at least about 25%" means removing the body fluid in the vascular system, as well as the free water present in and between individual cells. "Leaving water intact in an amount of at least from about 10 to about 20%" shall be taken to mean that after removal of water, the organ still contains a sufficient amount of water to permit later resuscitation, inclusive of the bound water in the living tissue.

When free water is removed from the tissues and cells of the organ, biostructures such as biomembranes become less susceptible to the attack of substances, particularly metal ions, that can be activated in the aqueous phase. The biostructures are presumably protected by the surrounding water in a crystalline state called "bound water". As a result of the removal of the polar medium that degrades the living tissue, the tissues and cells of the organ become immune to degradation with time and the organ can be preserved in a significantly improved state. In this case, trehalose in the preserving solution can contribute to stabilizing the biostructure.

The freshness of stored organs is believed to depend primarily on the amount of free water and to prolong the preservation period, it is theoretically preferred to remove free water as much as possible. To maintain resuscitability, it is preferred to ensure that water is left intact in a range of amounts that enable the maintenance of bound water. Bound water may be defined as the water in which the state of hydration or crystallization can be observed, and free water as the water other than bound water.

Animal organs are generally understood to have a water content in the range from about 60 to about 80 mass%. A suitable state of dehydration will depend on the inherent water content of a specific kind of organs but all that is required by the present invention is that the organ to be preserved should be deprived of water in an amount of at least about 25% by mass of the total weight of the organ before dehydration so that the organ contains water in an amount of at least about 10 to about 20% by weight of the total water content before dehydration.

If the method of the invention is to be applied to preserving heart, it comprises three steps, the first for removing blood from the heart by flushing with physiological saline until the blood in the heart is replaced by the physiological saline, the second for depriving the flushed heart of water in an amount of from about 25 to about 60% by weight of the total weight of the heart before dehydration, and the third for immersing the dehydrated heart in an inert medium and maintaining it in the state of apparent death at a chill temperature between about 2 and about 4° C. By removing about 25 to about 60% of water from the heart, water can be left intact in an amount of at least from about 10 to about 20% by weight of the total water content before dehydration.

Dehydration of organs can conveniently be accomplished by bringing the organ to be preserved into contact with a dehydrator and absorbing water from within the organ. Specifically, the washed and flushed organ is surrounded by the required amount of dehydrator and immersed in an inert, medium together with it. The immersed organ is gradually dehydrated in the inert medium until it suffers apparent death. Having been dehydrated to an extremely low water content, the organ stored cold in the inert medium can maintain chemical stability in all tissues including nerve tissue. In the experiments conducted by the present inventor, rat hearts could actually be preserved for as many as 10–20 days without suffering excessive damage to the nerve system.

In order to increase the resuscitation ratio and achieve further improvements in the state of preserved and resuscitated organs, a method of dehydration by withdrawing water from within the organ through channels in the vascular system may be employed in practicing the preservation method of the invention.

Specifically, this can be achieved by irrigation perfusion or flushing with a specified gas medium that can flow through arteries or veins connecting to capillaries in the organ until it displaces the water in the organ. The gas medium gets into capillaries from one end of the vascular system and creates a flow pressure that allows the gas medium to infuse all parts of the organ tissues at substantially the same rate; thereafter, the gas medium circulates through the capillaries (for example, from arterial to venous vessels) until it reaches the other end of the vascular system. As a result of this gas perfusion of the vascular system, the body fluid in the organ is pushed forward so that water is withdrawn from every one of the cells via capillaries. Gas perfusion can be effected with an irrigation apparatus for flushing physiological saline if the gas is pumped in instead of the physiological saline.

The gas to be supplied into the vascular system may be air or a gaseous mixture of $O_2$ and $CO_2$. Alternatively, inert gases may be used, as exemplified by $N_2$, He, Ar, Ne, Kr and Xe.

In anatomy, vascular systems are classified into two groups, blood vessels and lymphatics. For the purposes of the invention, nutrition blood vessels through which water and nutrients are supplied to individual cells in the organ of interest can preferably be used as the "vascular system". In the case of the heart, the irrigation apparatus may be connected to inherent vascular vessels leading to the atria and ventricles so that flow pressure is applied indirectly to the coronary arteries and veins leading to the nutrition blood vessels in the heart. Besides the nutrition vessel system, organs such as the liver have a functional blood vessel system associated with portal vein circulation; in such organs, the functional blood vessel system may be substituted for the nutrition vessel system.

Liquids to be supplied to the vascular system include solvents that make use of osmotic pressure difference to displace water from cells, as exemplified by hypertonic liquids more concentrated than the body fluids in organs. These may be substituted by the inert medium to be described later, or alcohols.

Dehydration via the vascular system utilizes the water supply passages inherent in organs and can hence create a uniform dehydrated state at slow speed in the desired tissues or cells. Even in the case of mammalian, multi-cell and multi-tissue organs, transfer to a highly dehydrated state can be achieved smoothly without undue stress on the living tissue. The living tissue is usually placed under stress by 25 mass % or more dehydration; however, dehydration via the vascular system can bring organs to apparent death in an extremely stable state without causing ischemic injury or damaging the living tissue. Upon refilling with water, functional resuscitation occurs not only in the cells and tissues but also in the organs themselves.

Apparent death usually means biological apparent death. The term "apparent death" as intended by the invention should be taken to mean such a state that the external signs of "life" are lost as a result of enhanced dehydration but can be restored upon refilling with water. The term "resuscitation" as used herein means such a phenomenon that upon refilling with water, a dehydrated tissue or organ resumes recognizable electrophysiological reactions or biological life activities, respectively.

In the method of the invention, the step of dehydration using gases is preferably preceded by blood removal using physiological saline. Blood removal is effective in avoiding the problem of blood coagulation upon contact with the flushing gas.

The "organ having a physiologically normal water content" is typically an organ as extracted from the living body. If the method of the invention includes the step of blood removal, this term can be taken to mean an organ whose blood has been replaced by physiological saline as a result of irrigation performed to effect blood removal. The degree of dehydration can be specified with reference to the weight of the "organ having a physiologically normal water content".

The physiological saline to be used in blood removal is a substitute body fluid having similar physiological activity to blood and typical examples are known Ringer's solutions such as KH (Kreps-Henseleit) solution. Polysaccharides that will help stabilize the dehydrated biostructure may be dissolved in physiological salines of this class. A preferred polysaccharide having this ability is trehalose. Other biostructure stabilizing substances that can be dissolved in physiological saline include malic acid, mannitol, glycerol, and amino acids such as glycine betaine, proline and ectoine.

The inert medium to be used in the invention is a medium that is insoluble in water and oils and fluorocarbons that are liquid at the temperature for preservation are preferred, with a liquid perfluorocarbon being particularly preferred. If similar conditions are satisfied, other forms of inert medium may be used such as gas, sol and gel. Other inert media that are believed to be useful include mercury and silicone oil.

The heart, liver, kidneys, pancreas and lungs preserved by application of the present invention can be resuscitated by flushing their vascular system with body fluid or substituted body fluids that have been warmed to near body temperature, as exemplified by the physiological saline described above, artificial blood and/or natural blood. The resuscitated organs or tissues collected from them are believed to be transplantable to the human body. Nerve tissue and other living tissues and cells can be collected from the resuscitated organs and used for testing purposes as in a pharmacological test.

Another possible application of the invention is to organs of mammals except humans that can be used as heterologous transplants to the human body and by this application the invention provides an effective technique for preserving animal organs that are expected to find increasing demand in clinical settings to deal with the shortage of human donors. In particular, the invention is also useful for preserving mass-producible organs such as the heart, liver and pancreas from cultured pigs; thus, the invention will provide an effective preservation technique that can withstand transport for a long time, particularly air transport for a period longer than ten-odd hours.

The invention will also find utility in application to the storage of tissues and organs that have been reconstituted by cultivating stem cells having totipotency such as embryonic stem cells taken from blatocysts. The invention may find further applicability to the storage of nerve tissues in the brain and other organs.

THE PREFERRED EMBODIMENT OF THE INVENTION

Step of blood removal

Figure 1:
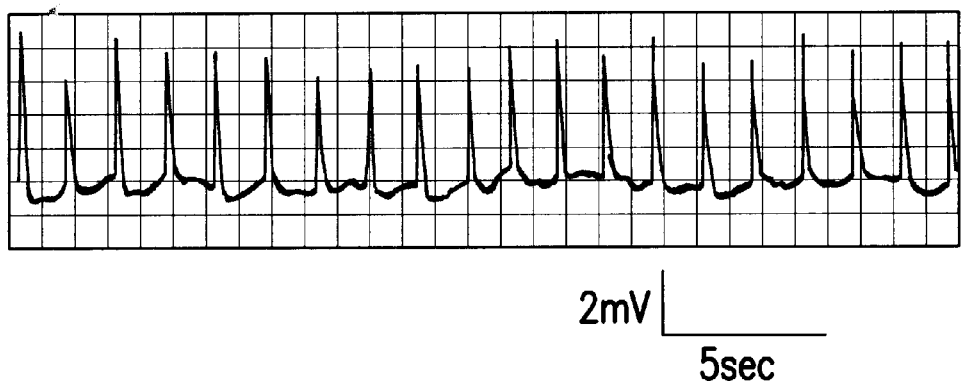
FIG. 1 is a surfacecardiac electrocardiogram (SECG) for an extracted rat R016 heart as resuscitated after 10-day preservation.

Upon contact with gases or exposure to low temperature, blood usually clots to form thrombi and this is an obstacle to the subsequent steps of dehydration and resuscitation. To eliminate this possibility, the organ to be preserved, for example, an organ extracted in surgery is washed to remove blood. The known Langendorff apparatus may be used to effect perfusion for blood removal. The technique of irrigation for blood removal is known to the skilled artisan as the Langendorff method (see Doring H. J. and Dehnert H.; Biomesstechnik-Verlag Match Gmb, Germany 1988). According to the Langendorff method, an irrigation catheter (or cannula) is attached to the aorta in the blood vessel system of the organ and a mixture of trehalose and KH solution is sent into the blood vessel system to replace the blood in the organ with the physiological saline. The physiological saline is preliminarily aerated to ensure that the organ is supplied at all times with a fresh substitute body fluid. During the blood removal by irrigation, the organ is cooled to 1–8° C. to stop its activity.

Step of Dehydration:

The step of blood removal is followed by dehydration.

i) Dehydration with Dehydrator

If dehydration is primarily performed using a dehydrator, a convenient way is by adjusting the dehydrator to a desired volume (which can remove water in an amount of at least 50% by weight of the total weight of the organ before dehydration) and immersing it in an inert medium (see below) together with the organ. Specifically, the organ as surrounded with silica gel, molecular sieve, zeolite or the like is placed in a metal cage, a synthetic fiber net or other casings that are made of materials neutral to the inert preserving medium, and then immersed in the inert medium.

The amount of the dehydrator to be used can be calculated from the percentage of water removal that is required by the organ of interest. After immersion in the inert medium, the dehydrator may be removed or replaced on a suitable timing; if necessary, an additional amount of the dehydrator may be added. If contacted by the dehydrator within the inert medium, the organ gets the internal water to be slowly absorbed by the dehydrator via the outer surface until the intended state of dehydrastion is reached.

ii) Dehydration Via the Vascular System

Dehydration with gas can be accomplished by means of the Langendorff apparatus used in the step of blood removal. For example, the aorta in the organ that has been subjected to the necessary blood removal is supplied with a suitable gas rather than physiological saline at a specified flow pressure from this irrigation apparatus. It will be readily understood by the skilled artisan that the artificial means of irrigation include not only a device for one-way supply of the gas through the aorta but also a closed circulation system connected between the aorta and venae cavae. Thus, the perfusion with gas is not limited to the forcing of the gas and it may be aspirated through the vascular system.

If the flow pressure created by the irrigation apparatus is applied to the vascular system of the organ, the physiological saline flows out of the organ through the venae cavae to cause progressive dehydration. Preferably, the gas entering blood vessels flow through individual capillaries toward the venae cavae and the water both within and between individual cells is forced under its own vapor pressure to enter the gas flowing through the blood vessels. Eventually, most of the free water within tissues and cells flows through the blood vessel system to be discharged to the outside of the organ.

Unlike the treatment by contact with the dehydrator, dehydration via the blood vessel system utilizes the extremely large surface area of the capillaries distributed uniformly in the organ, and the intended tissue and individual cells can be dehydrated in a fairly short period of time although slowly. This advantage is obvious from the smaller extent of unevenness in dehydration and from the by-no-means unbearable change in the color of the dehydrated organ. As will be shown in the examples to be given later in this specification, dehydration by irrigation with gas achieved markedly high resuscitation ratio, indicating significant improvements in the state of resuscitation. As further advantages, dehydration with gas is an active treatment that can be controlled externally, which puts less stress on organs that must be handled rapidly but carefully, and which is very efficient.

Inexpensive compressed gases packed in commercially available containers may be forced into the vascular system. In the case of an $O_2$—$CO_2$ gaseous mixture, the $CO_2$ content is preferably less than 5%. Dry gases were used in the Examples to be described later in this specification but humid gases may of course be used. More preferably, the dehydrating gas may be chosen from inert gases such as $N_2$, He, Ar, Ne, Kr and Xe. Among the inert gases, Xe is expensive but considering its reported anesthetic action on living tissues, the advantage of using Xe as the dehydrating gas would be great. The use of inert gases has the added advantage of avoiding damage that may be caused to living tissues by active oxygen.

The dehydration by perfusion with gas may be combined with the ancillary method of dehydration by bringing the organ into contact with a dehydrator. In the experiments the present inventor conducted using tardigrades, 100% resusictation was achieved when dehydration was performed in a highly humid environment, preferably at a humidity of 80%. Considering this fact, it would also be preferred to dehydrate organs at high humidity.

To give guide figures as the conditions for perfusion with gas, the aorta in the heart of a rat is perfused with air at a flow rate of ca. 0.05–0.2 $kgf/cm^2$ (ca. 4.9–19.6 kPa), preferably ca. 0.1 $kgf/cm^2$ (ca. 9.8 kPa), for a period of at least 1–1.5 hours. By means of perfusion with this amount of air, at least 25 mass % water removal can be achieved as contrasted with the total weight of the organ that is about to be dehydrated.

The organ about to be dehydrated contains the substitute body fluid and has a physiologically normal water content. For extended storage of the organ, the largest possible amount of free water must be removed. In the present invention, the amount of water to be removed is defined in terms of percent water removal (weight ratio) with reference to the total weight of the organ and expressed by the following equation:

Percent water removal (weight ratio)=100−[(total weight of the organ after dehydration/total weight of the organ before dehydration)×100]

The state of dehydration may be defined by other methods such as NMR which specifies the absolute amount or the state of the molecules of water present in the organ of interest. NMR is a technique most widely used by scientists to study the state of water in living tissues.

The first NMR-based study of the water in living tissues was reported by Belton, P. S., Jackson, R. R. and Packer, K. J. in Pulsed NMR Studies of Water in Strained Muscle, I. Transverse Nuclear Spin Relaxation Times and Freezing Effects; Biochem. Biophys. Acta. 286:16–25 (1972). A structural analysis of water by NMR was reported by Hazlewood, C. F., Chang, D. C., Woessner, D. E. and Nichols, B. C. in Nuclear Magnetic Resonance Transverse Relaxation Times of Water Protons in Skeletal Muscle; Biophys. J. 14:583–605 (1974).

Belton et al. concluded that the molecules of water in living tissues consisted of three states, ca. 8% of which was bound water, or water bound to biomolecules such as the intima of cell membranes, as well as proteins and nucleic acids, ca. 82% being free water, and the remaining 10% was occupied by free water bordering on the outside of cell membranes. The bound water differs from other molecules of water in that it has certain preferential orientations in several molecular layers based on the molecules of water directly bound to biopolymers.

Typically, it is understood that ca. 10–ca. 20% of the total water content in the living tissue is occupied by bound water and ca. 80–ca. 90% by free water. The total content of water in the heart of a rat is typically ca. 80 mass % of the total weight of the organ, so the contents of bound water and free water are respectively 8–16 mass % and 64–72 mass %.

In the step of dehydrating the heart of a rat, water is removed in an amount of ca. 25–60 mass % of the total weight of the organ and if this is the case, it is reasonable to think that all the water removed is free water. Hence, as the result of dehydration, the mass of the free water remaining in the rat's heart will drop to a level on the order of several to forty percent but the absolute amount of bound water remains the same. Although the actual water content slightly varies depending on the animal species and the type of the organ to be preserved, removing free water in an amount of at least ca. 25% by weight of the total weight of the organ before dehydration is sufficient to leave at least ca. 10–ca. 20% by weight of water (including bound water) intact on the basis of the total water content before dehydration.

While the percentage of free water removal that is tolerated by organs may vary with the type of the organ to be preserved, the intended duration of storage and other conditions for preservation, ca. 25–35% is currently considered safe for the heart of rats and if prolonged storage is intended, as much as ca. 45–50% of free water is preferably removed. Removing less than 25% of water makes little contribution to extending the duration of storage. Theoretically, removing water to a level near 60% where the presence of free water is very much limited would, make great contribution to extended storage.

As of today, no full explanation has been proposed for the mechanism connecting the above-described state of dehydration to the increase in the period of organ preservation. The present inventor has at least shown that the increase in the period of organ preservation does not depend on the composition of the preserving fluid but depends largely on the absolute amount of water molecules in the tissues or cells of the organ. Since the organ that ceased to show signs of substantial life activity as the result of dehydration of its tissues and cells later resuscitated, the organ may well he considered to have reached "apparent death", which may be called "immortal state"or more academically "cryptobiotic state" (Vreeland H. R. et al; Nature, Vol. 407, pp. 897–900, Oct. 19, 2000: Cano J. R. et al.; Science, Vol. 268, pp. 1060–1064, May 19, 1995).

Step of Preservation

The dehydrated organ is preserved in a perfluorocarbon which is an inert medium insoluble in water and oils. The organ is immersed in the inert medium generally in a closed state at atmospheric pressure, optionally under superatmospheric pressure. As already mentioned, the organ may be immersed in the inert medium together with the dehydrator. The inert medium is preferably aerated with pure oxygen.

The term "at a chill temperature or below" as used herein means the range of from ca. +1 to ca. +8° C., preferably in the neighborhood of ca. +2 to ca. +4° C. The organ is maintained in this preserved state for a predetermined number of days. If the free water in the organ is adequately removed, it can theoretically be stored frozen as in liquid nitrogen.

Step of Resuscitation

To resuscitate the organ from the preserved state, the already mentioned Langendorff method can be employed. First, the preserved organ is taken out of the perfluorocarbon and the dehydrator, if any, is also removed. The organ is then immersed in a KH solution, preferably aerated with pure oxygen, within a Petri dish at +4° C. A perfusion catheter is fixed to the aorta in the organ and the KH solution, preferably aerated continuously with a gaseous mixture of $O_2$ and $CO_2$ and warmed to 37° C., is forced by an irrigation pump into the catheter at a constant flow rate. The organ is resuscitated by this procedure of irrigation.

Verification of Resuscitation:

One of the important aspects of preserving mammalian organs is the need for post-storage verification of viable tissues in the organ. This can be accomplished by several methods including tissue autopsy, actual transplant and electrophysiology. Whichever method is adopted, it must be determined whether each type of tissue cell is alive. In the present invention, electrophysiological verification of tissue cell resuscitation was conducted by taking SECGs because they could provide real-time recording of the activity of nerve cell tissue and cell death could be found to have occurred at the point in time when neuron activity disappeared. As an ancillary means, the visual change in the color of the organ tissues and the presence of beats (in the case of the heart) were monitored to complete the verification of organ resuscitation.

The following examples are provided for the purpose of further illustrating the present invention but are in no way to be taken as limiting.

EXAMPLE 1

Seven-week old male Wistar rats (300 g) were artificially reproduced in compliance with the American NIH standards for laboratory animals. The rats were anesthetized with Nembutal (Na solution) and their SECGs were recorded. Thereafter, the heart was extracted from each animal, immersed in a KH solution aerated with pure oxygen and mixed with 117 mmol of trehalose and had the adhering blood rinsed off. Moisture was only wiped off from the outer surface of the heart before its total weight was measured.

Catheters were inserted into the aorta and vena cavae in the extracted heart and the same KH solution mixed with trehalose was irrigated through the heart to remove blood. Silica gel (9–10 g sufficient to remove nearly 60% of the water in the heart) was put into a ball-shaped metal cage and the pretreated heart was placed on the silica gel, immersed in a liquid perfluorocarbon (C8F17; FLUORINERT FC77 of Sumitomo 3M) at 4° C. which had been aerated with pure oxygen for one minute; the heart was then placed in a hermetically sealed 500-mL jar and stored in a refrigerator.

After 10 days, the heart was recovered from the preservation fluid; after removing the silica gel with tweezers, the recovered heart was placed in a KH solution in a Petri dish at 4° C. A catheter for perfusion was attached to the aorta with cotton thread and the heart was set in a fixed-flow Langendorff perfusion apparatus. A KH solution continuously aerated with a gaseous mixture of $O_2$ and $CO_2$ at a volume ratio of 95:5 was supplied from the storage tank, warmed to 37° C. within the glass coil tube in the homothermal tank and forced by an irrigation pump (Masterflex Model No. 7520–10 of Cole-Palmer Instrument Co.) into the aortic catheter at a constant flow rate of 6 mL/g (heart's weight) per minute.

As is well known, isolated hearts resuscitate spontaneously and nerve response appears if the tissue cells are alive. Irrigation of the extracted hearts was started at predetermined temperatures and SECG electrodes were attached at the left ventricle and the opening of the aorta, and with a bipolar lead, SECGs were recorded continuously using an organic amplifier (Bioview-E of NEC-Sanei). This sequence of treatments and operations was specifically applied to the following experiments.

i) Experiment 1

At 15:10 on Jul. 7, 1998, an R016 rat under Nembutal anesthesia was incised in the chest to recover the heart which was subjected to irrigation for removing blood. Upon completion of this preliminary treatment, the extracted heart weighed 1.240 g.

Ten days later (Jul. 16, 1998), the heart was recovered from the preserving perfluorocarbon fluid at 4° C. and had the silica gel removed at 17:20; just before irrigation started, the heart weighed 0.774 g. During the storage, about 38% of the water in the cells of the heart tissue had been absorbed by the silica gel.

Thereafter, a catheter was inserted into the aorta of the heart and fastened with cotton thread. The heart was then set in the fixed-flow Langendorff irrigation apparatus and irrigation started at 17:25 at 37° C. The heart resuscitated to give the SECG shown in FIG. 1 (recorded at 18:31 with 40 beats per minute). The heart rate later dropped to 27 beats per minute at 18:47.

ii) Experiment 2

At 17:30 on Jul. 10, 1998, an R020 rat was incised in the chest to recover the heart which was subjected to irrigation for removing blood. Upon completion of this preliminary treatment, the extracted heart weighed 1.521 g.

Twenty days later (Jul. 30, 1998), the heart was recovered from the preservation fluid and had the silica gel removed at 15:12; just before irrigation started, the heart weighed 1.063 g. During the storage, about 30% of the water in the cells of the heart tissue had been absorbed by the silica gel.

Figure 2:
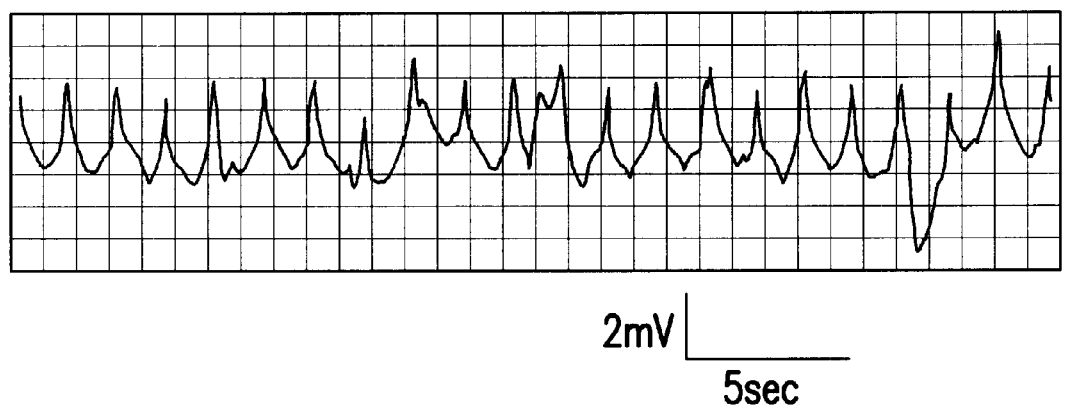
FIG. 2 is an SECG for an extracted rat R020 heart as resuscitated after 20-day preservation.

Thereafter, a catheter was inserted into the aorta of the heart and fastened with cotton thread. The heart was then set in the fixed-flow Langendorff irrigation apparatus and irrigation started at 15:13 at 32° C. The heart resuscitated to give the SECG shown in FIG. 2 (recorded at 15:19 with 42 beats per minute).

iii) Experiment 3

At 14:40 on Jul. 26, 1998, an R029 rat was incised in the chest to recover the heart which was subjected to irrigation for removing blood. Upon completion of this preliminary treatment, the extracted heart weighed 1.291 g.

Ten days later (Aug. 5, 1998), the heart was recovered from the preservation fluid and had the silica gel removed at 16:55; just before irrigation started, the heart weighed 0.832 g. During the storage, about 36% of the water in the cells of the heart tissue had been absorbed by the silica gel.

Figure 3:
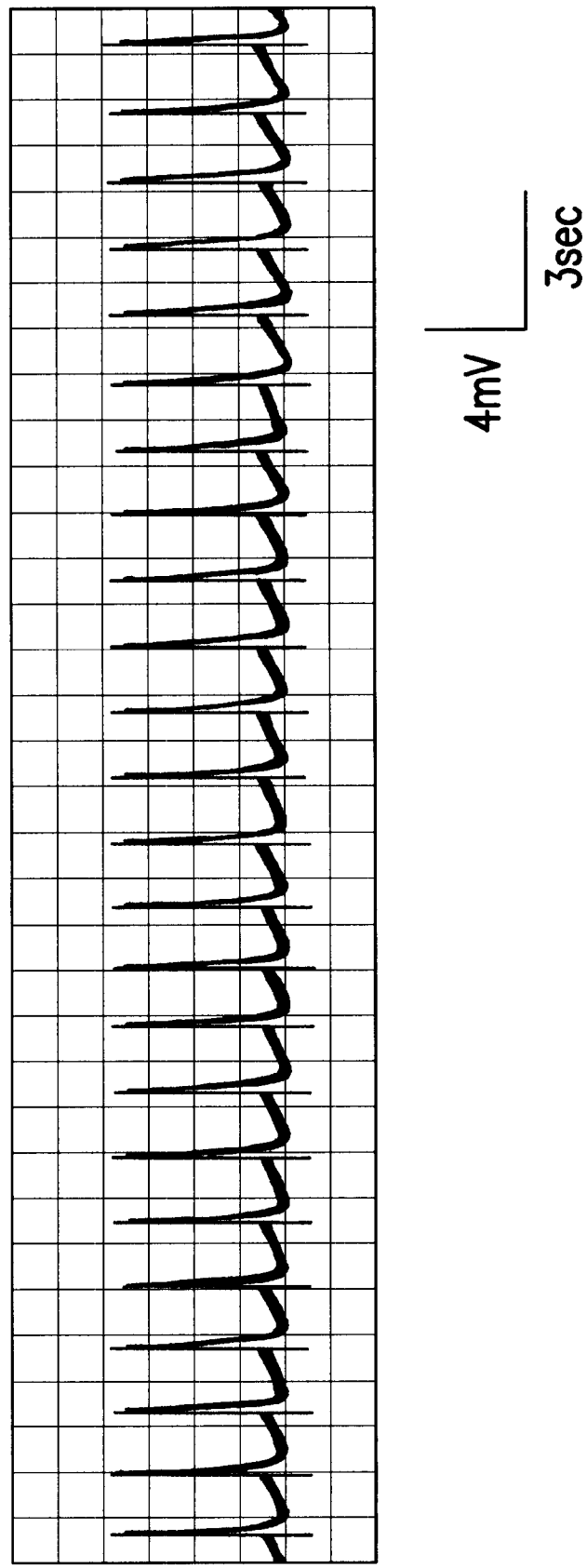
FIG. 3 is an SECG for an extracted rat R029 heart as resuscitated after 10-day preservation.

Thereafter, a catheter was inserted into the aorta of the heart and fastened with cotton thread. The heart was then set in the fixed-flow Langendorff irrigation apparatus and irrigation started at 17:19 at 34° C. The heart resuscitated to give the SECG shown in FIG. 3 (recorded at 17:39 with 42 beats per minute). The activity of the heart was also visible.

iv) Experiment 4

At 14:40 on Jul. 29, 1998, an R033 rat was incised in the chest to recover the heart which was subjected to irrigation for removing blood. Upon completion of this preliminary treatment, the extracted heart weighed 1.293 g.

Ten days later (Aug. 7, 1998), the heart was recovered from the preservation fluid and had the silica gel removed at 15:58; just before irrigation started, the heart weighed 0.808 g. During the storage, about 38% of the water in the cells of the heart tissue had been absorbed by the silica gel.

Figure 4:
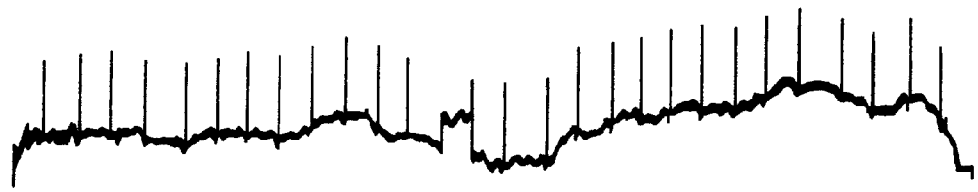
FIG. 4 is an SECG for an extracted rat R033 heart as resuscitated after 10-day preservation.

Thereafter, a catheter was inserted into the aorta of the heart and fastened with cotton thread. The heart was then set in the fixed-flow Langendorff irrigation apparatus and irrigation started at 16:15 at 36° C. The heart resuscitated to give the SECG shown in FIG. 4 (recorded at 16:19 with 108 beats per minute). As in Experiment 3, the activity of the heart was also visible.

v) Experiment 5

At 16:01 on Jul. 29, 1998, an R034 rat was incised in the chest to recover the heart which was subjected to irrigation for removing blood. Upon completion of this preliminary treatment, the extracted heart weighed 1.375 g.

Ten days later (Aug. 7, 1998), the heart was recovered from the preservation fluid and had the silica gel removed at 17:48; just before irrigation started, the heart weighed 0.808 g. During the storage, about 38% of the water in the cells of the heart tissue had been absorbed by the silica gel.

Figure 5:
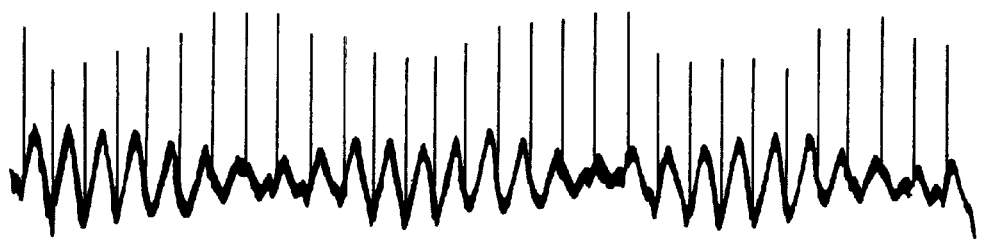
FIG. 5 is an SECG for an extracted rat R034 heart as resuscitated after 10-day preservation.

Thereafter, a catheter was inserted into the aorta of the heart and fastened with cotton thread. The heart was then set in the fixed-flow Langendorff irrigation apparatus and irrigation started at 17:57 at about 30° C. The heart resuscitated to give the SECG shown in FIG. 5 (recorded at 18:11 with 66 beats per minute).

vi) Experiment 6

At 14:30 on Aug. 1, 1998, an R041 rat was incised in the chest to recover the heart which was subjected to irrigation for removing blood. Upon completion of this preliminary treatment, the extracted heart weighed 1.295 g.

Eleven days later (Aug. 12, 1998), the heart was recovered from the preservation fluid and had the silica gel removed at 17:40; just before irrigation started, the heart weighed 0.797 g. During the storage, about 39% of the water in the cells of the heart tissue had been absorbed by the silica gel.

Figure 6:
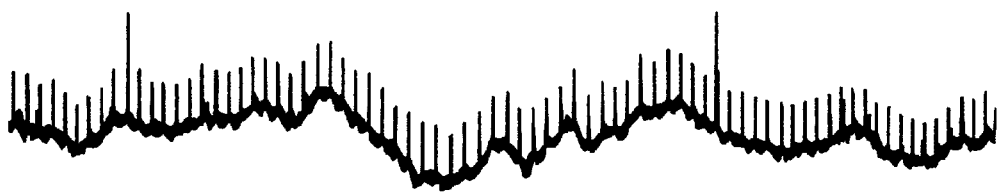
FIG. 6 is an SECG for an extracted rat R041 heart as resuscitated after 11-day preservation.

Thereafter a catheter was inserted into the aorta of the heart and fastened with cotton thread. The heart was then set in the fixed-flow Langendorff irrigation apparatus and irrigation started at 17:56 at 36° C. The heart resuscitated to give the SECG shown in FIG. 6 (recorded at 18:13 with 162 beats per minute).

vii) Reference Experiment

At 13:16 on Jul. 20, 1998, an R051 rat was incised in the chest to recover the heart which was subjected to irrigation for removing blood. Upon completion of this preliminary treatment, the extracted heart weighed 1.162 g.

Thereafter, a catheter was inserted into the aorta of the heart and fastened with cotton thread. The heart was then set in the fixed-flow Langendorff irrigation apparatus and irrigation started at 13:25 to give the SECGs shown in FIG. 7A (recorded at 13:45 with 171 beats per minute; irrigation temperature, 34° C.), FIG. 7B (recorded at 17:25 with 161 beats per minute; irrigation temperature, 32° C.), FIG. 7C (recorded at 19:25 with 134 beats per minute; irrigation temperature, 32.1° C.), and FIG. 7D (recorded at 22:02 with 17 beats per minute; irrigation temperature, 31.1° C.). At the points in time when the SECG showed an amplitude (output) of 4 mV per centimeter, the vigorous activity of the heart was visible. At 22:22, no potential appeared, indicating the cessation of neuron activity.

Figure 7:
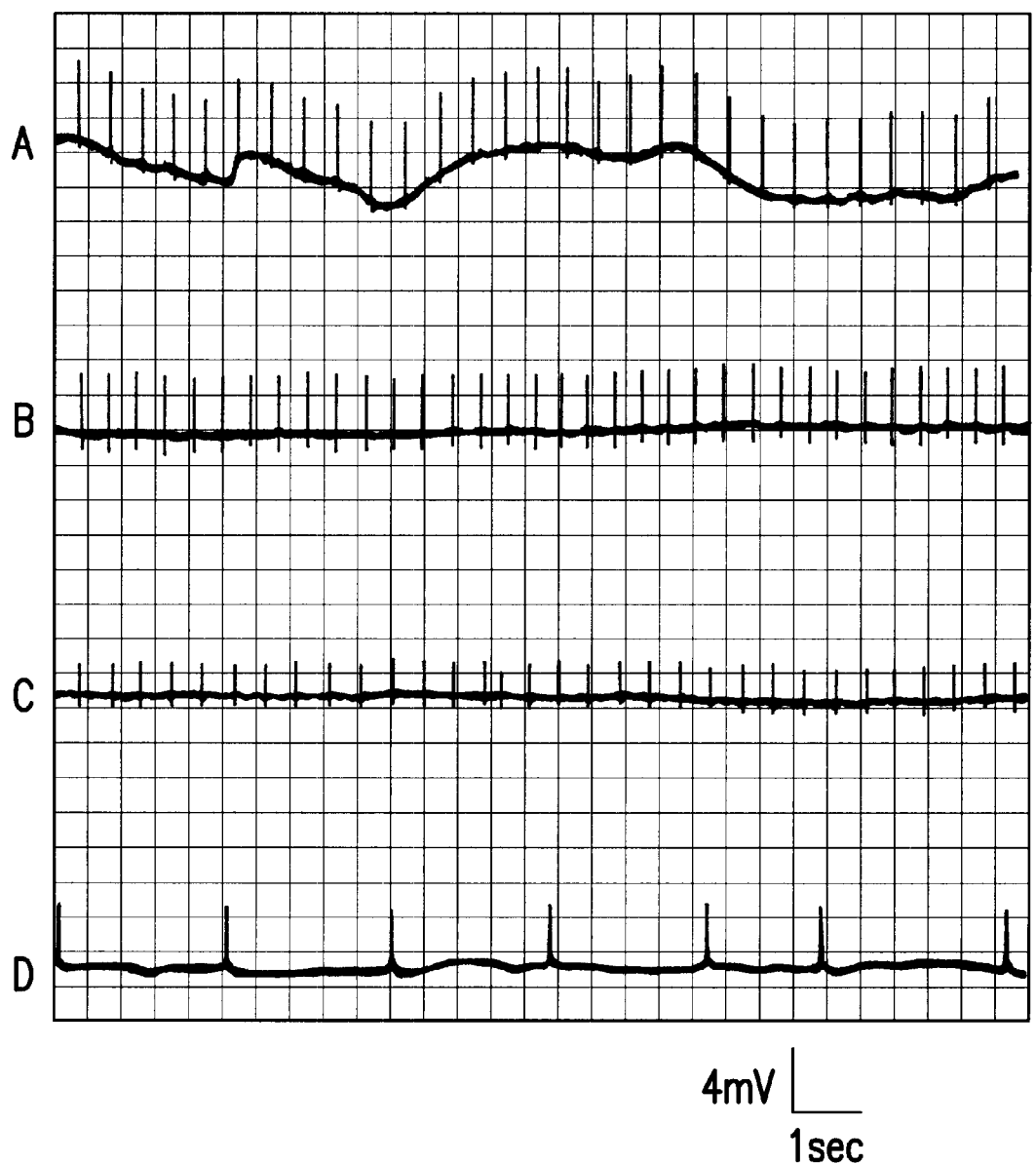
FIG. 7 is an SECG recording for an extracted rat R051 heart as a comparison.

The SECGs shown in FIGS. 1–6 which were recorded after storage for 10–20 days had amplitudes (outputs) of 2–4 mV which were of the same order as the amplitude of the SECG shown in FIG. 7 for the control experiment. Thus, even after 10to 20-day storage, the heart produced comparable outputs to the value at which the vigorous activity of the heart was visible in the control experiment and this indicates the absence of excessive damage to the nerve system in the preserved heart.

EXAMPLE 2

Rats were administered Nembutal (0.25 mL) and heparin sodium salt (5 mg) by intraperitoneal injection. After measurement of their body weight, the heart was extracted from each animal. The extracted heart was placed in a homothermal tank and a catheter was inserted into the aorta; thereafter, using a KH solution mixed with trehalose (117 mmol) and aerated with a gaseous mixture of 95% $O_2$ and 5% $CO_2$, irrigation for blood removal was performed by the Langendorff method. The temperature of the homothermal tank was lowered to stop the beating of the heart, thereby completing the process of blood removal by irrigation. After measuring the weight of the heart, the same irrigation apparatus was used to feed the gaseous mixture of 95% $O_2$ and 5% $CO_2$ into the heart, thereby starting dehydration. While monitoring the percent water removal as calculated from the measurements of heart's weight, dehydration was continued for about 1 hour and a half, whereupon the gas irrigation was stopped. After measuring its weight, the heart was immersed in a liquid perfluorocarbon aerated with the gaseous mixture of $O_2$ and $CO_2$. After the passage of a predetermined time, the preserved heart was taken out of the liquid perfluorocarbon. A catheter was inserted into the aorta of the heart and an attempt was made to resuscitate the heart by Langendorff irrigation using a warm KH solution aerated with the gaseous mixture of $O_2$ and $CO_2$.

i) Experiment 7
R349 (5-week old male Wistar rat): Storage for 4 hours Sept. 11, 2000 at 24° C.
15:39 body weight measured: 130 g
15:51 extraction of the heart started
15:53 extraction of the heart and insertion of catheter ended
15:53 blood removal by irrigation started: homothermal tank held at 5.0° C. and irrigation effected at flow rate of 1.0–3.8 mL/min
16:14 the heart stopped beating and blood removal by irrigation ended: homothermal tank held at 5.0° C. and the heart was at 18.2° C.
16:14 heart's weight measured: 0.663 g
16:18 dehydration started by irrigation with $O_2/CO_2$: gas pressure at 0.05 kgf/cm$^2$ and homothermal tank held at 2.8° C.
16:48 heart's weight measured: 0.516 g at 22.2% water removal
16:50 dehydration continued: gas pressure at 0.05 kgf/cm$^2$ and homothermal tank held at 1.1° C.
17:20 heart's weight measured: 0.458 g at 30.9% water removal
17:21 dehydration continued: gas pressure at 0.05 kgf/cm$^2$ and homothermal tank held at 1.6° C.
17:51 heart's weight measured: 0.394 g at 40.6% water removal
17:55 4-hr storage in PFC: 0.6° C.
21:54 storage ended and the heart recovered at 26° C.
21:55 heart's weight measured: 0.436 g
21:55 irrigation for resuscitation started: homothermal tank held at 34.4° C. and irrigation effected at flow rate of 1.0–3.8 mL/min
23:40 irrigation for resuscitation ended: homothermal tank held at 33.7° C.

Assessment: Faint contraction of the cardiac muscle occurred at 4 minutes after the start of KH irrigation but there was no atrial movement. The cardiac muscle continued to move until the irrigation was stopped. The heart swelled slightly.

ii) Experiment 8
R350 (5-week old male Wistar rat): Storage for 8 hours Sept. 12, 2000 at 25° C.
19:10 body weight measured: 150 g
19:20 extraction of the heart started
19:22 extraction of the heart and insertion of catheter ended
19:22 blood removal by irrigation started: homothermal tank held at 5.0° C. and irrigation effected at flow rate of 1.0–3.8 mL/min
19:37 the heart stopped beating and blood removal by irrigation ended: homothermal tank held at 4.6° C. and the heart was at 15.7° C.
19:39 heart's weight measured: 0.718 g
19:43 dehydration started by irrigation with $O_2/CO_2$: gas pressure at 0.1 kgf/cm$^2$ and homothermal tank held at 4.4° C.
20:13 heart's weight measured: 0.647 g at 9.9% water removal
20:15 dehydration continued: gas pressure at 0.1 kgf/cm$^2$ and homothermal tank held at 2.4° C.
20:35 heart's weight measured: 0.550 g at 23.4% water removal
20:48 dehydration continued: gas pressure at 0.05 kgf/cm$^2$ and homothermal tank held at 4.8° C.
20:18 heart's weight measured: 0.483 g at 32.7% water removal
17:55 8-hr storage in PFC: 0.6° C. Sep. 13, 2000
05:21 storage ended and the heart recovered at 27° C.
05:23 heart's weight measured: 0.523 g
05:24 irrigation for resuscitation started: homothermal tank held at 33.6° C. and irrigation effected at flow rate of 1.0–3.8 mL/min
07:25 irrigation for resuscitation ended: homothermal tank held at 36.6° C.

Assessment: Starting at 05:29, the cardiac muscle contracted vigorously but that event stopped in about 10 seconds. Around 06:00, the right side of the heart was found to move faintly in the area near the pulmonary artery. The heart swelled considerably and from appearances it was hardly found beating; however, when the irrigation was stopped and the heart was drained of the KH solution, distinct beating was observed.

iii) Experiment 9
R350 (5-week old male Wistar rat): Storage for 16 hours Sept. 13, 2000 at 245° C.
16:22 body weight measured: 120 g
16:28 extraction of the heart started
16:31 extraction of the heart and insertion of catheter ended
16:31 blood removal by irrigation started: homothermal tank held at 26.9° C. and irrigation effected at flow rate of 1.0–3.8 mL/min
16:44 the heart stopped beating and blood removal by irrigation ended: homothermal tank held at 4.6° C. and the heart was at 16.2° C.
16:45 heart's weight measured: 0.605 g
16:50 dehydration started by irrigation with $O_2/CO_2$: gas pressure at 0.1 kgf/cm$^2$ and homothermal tank held at 3.3° C.
17:20 heart's weight measured: 0.534 g at 11.7% water removal
17:23 dehydration continued: gas pressure at 0.1 kgf/cm$^2$ and homothermal tank held at 1.3° C.

17:53 heart's weight measured: 0.517 g at 14.5% water removal
17:55 dehydration continued: gas pressure at 0.2 kgf/cm² and homothermal tank held at 0.5° C.
18:25 heart's weight measured: 0.522 g at 13.7% water removal
18:30 16-hr storage in PFC: 2.8° C. Sep. 14, 2000
10:28 storage ended and the heart recovered at 25° C.
10:30 irrigation for resuscitation started: homothermal tank held at 32.9° C. and irrigation effected at flow rate of 1.0–3.8 mL/min
17:25 irrigation for resuscitation ended: homothermal tank held at 34.5° C.

Assessment: The heart swelled so extensively that the state of its beating was not clear at all and this made the recording of an SECG necessary.

EXAMPLE 3

An experiment for the resuscitation of the rat's heart was performed as in Example 2, except that dehydration was effected by flushing with air and that the duration of storage was extended to 24 hours.

i) Experiment 10
Rat R443 Feb. 6, 2001
16:10 the heart extracted
16:20 blood removal by irrigation started: homothermal tank first held at 26.8° C. and ended at 7.9° C.
16:45 blood removal by irrigation ended and hearts weight measured: 0.582 g
16:45 the heart was immersed in PFC as it was flushed with air (0.1 kgf/cm²) through the aorta Feb. 7, 2001
16:48 the heart recovered from PFC
16:50 heart's weight measured: 0.430 g at 26.1% water removal
16:50 irrigation with KH solution started: homothermal tank first held at 27.0° C. and ended at 35.5° C.
18:30 the heart was found to resuscitate with consistent beasting ii) Experiment 11
Rat R444 Feb. 7, 2001
18:55 Nembutal (0.2 mL) administered
18:57 heparin sodium (5 mg) administered
18:57 body weight measured
19:00 the heart extracted
19:03 flushing with trehalose in KH solution started: homothermal tank first held at 27.6° C. and ended at 5.5° C.
19:23 irrigation ended and heart's weight measured: 0.767 g
19:27 flushed with air in jar (0.1 kgf/cm², 0.8° C.)
19:57 irrigation ended and heart's weight measured: 0.483 g at(34.8% water removal
20:00 the heart immersed in PFC Feb. 8, 2001
20:25 the heart recovered from PFC (0.5° C.)
20:27 heart's weight measured
20:27 flushing with KH solution started: homothermal tank first held at 26.9° C. and ended at 35.4° C.
21:27 the heart was found to resuscitate and beat several times before coming to complete stop

EXAMPLE 4

Five-week old male Wistar rats were reproduced in compliance with the American NIH standards for laboratory animals. Five rats were used in each of the following experiments. Perfluorocarbon (PFC) was used as an inert medium.

i) Experiment 12 (4-hr storage)
The rats were administered intraperitoneally first with Nembutal (0.2 mL), then with a solution of heparin sodium (5 mg) in physiological saline (0.3 mL). Each rat was incised in the chest and the heart was removed. A catheter was inserted into the aorta of the heart and ligated with cotton thread. The heart was then set on a fixed-flow perfusion apparatus and flushed with a KH solution having trehalose (117 mmol) dissolved therein; the irrigation temperature was 27° C. and the flow rate of the KH solution was 3.2 mL/min. The KH solution was constantly aerated with a gaseous mixture of 95% $O_2$ and 5% $CO_2$. The temperature of the flushing fluid was gradually lowered until the heart stopped beating. After measuring the its weight, the heart was dried by flushing with air gas through the catheter at a flow rate of 0.1 kgf/cm². After measuring its weight, the dry heart was preserved within PFC held at 4° C. as it was constantly aerated with an $O_2/CO_2$ mixture. After 4 hours, the heart was taken out of the preservation fluid, set on the fixed-flow irrigation apparatus and flushed with a KH solution as it was constantly aerated with an $O_2/CO_2$ mixture; the temperature of the KH solution was 27° C. and it was flushed at a flow rate of 3.2 mL/min. As is well known, when the preserved heart is subjected to another irrigation, it will resuscitate spontaneously and neuron activity will appear if the tissue cells are still alive. Electrodes were attached to the resuscitated heart and an SECG was recorded with a pen oscillograph.

ii) Experiment 13 (16-hr storage)
The procedure of Experiment 12 was repeated except that the duration of storage was extended to 16 hours.

The time of gas irrigation and the percent water removal achieved for each rat are shown below.

| | | |
|---|---|---|
| Experiment 12 | 1-1 | 1 hr and 34 min, 44.1% |
| | 1-2 | 2 hr and 37 min, 32.8% |
| | 1-3 | 2 hr and 37 min, 44.4% |
| | 1-4 | 2 hr and 37 min, 47.5% |
| | 1-5 | 3 hr and 7 min, 41.1% |
| Experiment 13 | 2-1 | 1 hr and 35 min, 44.4% |
| | 2-2 | 2 hr and 37 min, 41.2% |
| | 2-3 | 1 hr and 3 min, 45.8% |
| | 2-4 | 3 hr and 12 min, 41.3% |
| | 2-5 | 2 hr and 9 min, 41.4% |

Result: The resuscitation ratio was 100% in both Experiments 12 and 13.

In each of Experiments 12 and 13, there were significant variations in the relationship between the time taken to remove water and the actual percent water removal. A probable reason is that one extracted heart had a different state from another sample. Air as supplied through the catheter inserted into the aorta would pass through the openings of the right and left coronary arteries to fill the capillaries in the cardiac muscle, thereby drying its cells. However, if the slightest thrombus formation occurs in capillaries, the air gas will not reach the cells farther ahead; this would be the reason for the lack of proportionality between the time taken to remove water and the actual percent water removal. Whatever the reason, it was quite surprising that the hearts of rats deprived of water at 40% or more resuscitated at 100% probability after preservation for 4 or 16 hours.

What is claimed is:
1. A method for preserving mammalian organs, comprising the steps of:
   dehydrating an organ to remove water in an amount of at least 25% by weight of the total weight of the organ before dehydration but leave intact an amount of water that permits later resuscitation, wherein the dehydration includes feeding a gas into the vascular system in the organ;

immersing said dehydrated organ in an inert medium; and maintaining said dehydrated organ at a chill temperature between 1° C. and 8° C.

2. A method for preserving mammalian organs, comprising the steps of:

dehydrating an organ having a physiologically normal water content in an amount of at least 25% by weight of the total weight of the organ before dehydration such that at least 10% of the total content of water before dehydration is left after dehydration, wherein the dehydration includes feeding a gas into the vascular system in the organ;

immersing the dehydrated organ in an inert medium; and maintaining said dehydrated organ at a chill temperature between 1° C. and 8° C.

3. A method for preserving a mammalian heart, comprising the steps of:

removing blood from the heart by flushing said heart with saline solution until said blood in the heart is replaced by said saline solution; dehydrating the flushed heart of water in an amount of at least 25% but not more than 60% of the total weight of the heart before dehydration, wherein the step of dehydration includes feeding a gas into the vascular system of the heart;

immersing the dehydrated heart in an inert medium; and maintaining said dehydrated heart in said inert medium at a chill temperature between 1° C. and 8° C.

4. The method of preservation according to claim 1, wherein said step of dehydration includes bringing a dehydrator into contact with the organ.

5. The method of preservation according to claim 1, wherein said step of dehydration includes withdrawing water from within the organ through channels in the vascular system in said organ.

6. The method of preservation according to any one of claims 1 to 3, wherein said gas is an $O_2$-based gaseous mixture of $O_2$ and $CO_2$.

7. The method of preservation according to claim 3, wherein the gas is flushed into the aorta of the heart and the resulting flow of said gas is used to withdraw water from within blood vessels.

8. The method of preservation according to any one of claims 1 to 3, wherein a stabilizing ingredient is dissolved in said inert medium and said stabilizing ingredient is trehalose.

9. The method of preservation according to any one of claims 1 to 3, wherein a liquid perfluorocarbon is used as said inert medium.

10. The method of preservation according to any one of claim 1 or 2, wherein said organ is selected from the group consisting of the heart, liver, kidneys, pancreas and lungs.

11. A method for organ transplantation comprising the steps of:

resuscitating an organ preserved by the method according to claim 1 by irrigating the vascular system in either of said organs with body fluid or a substitute body fluid, each being near body temperature; and transplanting said resuscitated organ into the human body.

12. The method of claim 3, wherein said saline solution is physiological saline.

13. The method of claim 1, 2 or 3, wherein said chill temperature is between 2 and 4° C.

* * * * *